United States Patent
Diers et al.

(10) Patent No.: US 7,833,013 B2
(45) Date of Patent: Nov. 16, 2010

(54) DEVICE, METHOD AND KIT FOR DETERMINING ORTHODONTIC DIMENSIONS

(76) Inventors: Nelson R. Diers, 9975 Lakewood La., Cincinnati, OH (US) 45242; N. Todd Diers, 9975 Lakewood La., Cincinnati, OH (US) 45242

( * ) Notice: Subject to any disclaimer, the term of this patent is extended or adjusted under 35 U.S.C. 154(b) by 617 days.

(21) Appl. No.: 11/609,961

(22) Filed: Dec. 13, 2006

(65) Prior Publication Data

US 2008/0145811 A1  Jun. 19, 2008

(51) Int. Cl.
*A61C 19/04* (2006.01)

(52) U.S. Cl. .......................... 433/72; 351/204

(58) Field of Classification Search ............... 433/72, 433/73, 26; 351/204; 33/512, 513
See application file for complete search history.

(56) References Cited

U.S. PATENT DOCUMENTS

| | | | |
|---|---|---|---|
| 716,516 A * | 12/1902 | Boothroyd et al. ............ 33/200 |
| 1,052,161 A * | 2/1913 | Mayerle ..................... 33/200 |
| 1,505,447 A * | 8/1924 | Uhlemann ................... 33/200 |
| 1,505,792 A * | 8/1924 | Ludlum ..................... 433/72 |
| 1,662,670 A * | 3/1928 | Harter ...................... 33/514 |
| 1,804,749 A * | 5/1931 | Desmond .................... 33/200 |
| 2,887,008 A | 5/1959 | Gross |
| 4,229,164 A | 10/1980 | Robnett |
| 4,416,063 A | 11/1983 | Nestor et al. |
| 4,768,953 A | 9/1988 | Nestor et al. |
| 4,892,480 A * | 1/1990 | Levandoski ................. 433/73 |
| 5,187,503 A | 2/1993 | Hilton |
| 5,560,607 A | 10/1996 | Macroglou |
| 5,659,625 A | 8/1997 | Marquardt |
| 5,867,588 A | 2/1999 | Marquardt |
| 5,951,498 A | 9/1999 | Arnett |
| 6,109,917 A * | 8/2000 | Lee et al. ................... 433/73 |
| 6,261,248 B1 * | 7/2001 | Takaishi et al. ............. 600/590 |
| 6,413,085 B1 | 7/2002 | Lee |
| 6,821,116 B2 | 11/2004 | Severence |
| 7,699,607 B2 * | 4/2010 | Margossian ................. 433/73 |
| 2005/0214710 A1 | 9/2005 | Erskine-Smith |

\* cited by examiner

*Primary Examiner*—Ralph A Lewis
(74) *Attorney, Agent, or Firm*—Hasse & Nesbitt LLC; Ronald J. Richter; Daniel F. Nesbitt

(57) ABSTRACT

A device, method and kit for determining suitable orthodontic/dental dimensions for an individual's teeth as they relate to facial landmarks. The orthodontic dimensions are determined according to the Golden Proportion. The measuring device can be a pair of modified eyeglasses having a gauge thereon in the form of a transparent ruler body with a center marking line, or the measuring device can be a measuring grid having a center marking line and peripheral marking lines superimposed over a photograph of an individual's face. Peripheral marking lines are spaced at standard distances from the right and left of the center marking line. An orthodontist trained to use the invention can use the orthodontic dimensions for an individual in a treatment plan to alter the individual's teeth, to modify their function, or to improve their cosmetic appearance. The device can also be part of a kit for determining a suitable size and position for an individual's teeth as they relate to facial landmarks.

5 Claims, 4 Drawing Sheets

DEVICE, METHOD AND KIT FOR DETERMINING ORTHODONTIC DIMENSIONS

FIELD OF THE INVENTION

This invention relates to the field of orthodontics and dentistry and, more particularly, to a device, method and kit for measuring facial parameters for use in orthodontic and dental analysis.

BACKGROUND OF THE INVENTION

Orthodontics is the branch of dentistry dealing with tooth and jaw irregularities and their related structures. The primary purpose of orthodontic treatment is to alter the position of an individual's teeth and jaws, and to reorient these structures in order to modify their cosmetic appearance and/or improve their function. Techniques for orthodontics have become extremely sophisticated over the years.

When considering orthodontic treatment for a particular individual, typically the individual's tooth size and jaw dimension are accepted as they are, and the orthodontist has not traditionally attempted cosmetic change based upon the individual's facial parameters. Rather, the orthodontist typically uses a wax imprint of the individual's teeth and then attempts to straighten or re-align the teeth with braces and/or other currently known orthodontic devices.

A common principal relating to what is considered "beautiful" is the universal recognition of pleasant proportion. Early Greek mathematicians recognized this, and described what has been called the "Golden Proportion" or the "Golden Ratio." This proportion, typically indicated with the Greek letter $\Phi$, has long been used by artists, architects, and other scholars to create aesthetically pleasing works of art and structures. In short, the Golden Proportion is a mathematical relationship between two linear distances from the division of a straight line in such a way that the shorter part (S) is to the longer part (L) as the longer part is to the whole (S+L), such that each ratio equals 0.618. That is, $S/L=L/(S+L)=0.618$. When this relationship applies, then the ratio of L to S is 1.618, or approximately 89/55.

The Golden Proportion has been recognized as describing an aesthetically pleasing relationship between the sizes of the frontal upper teeth when viewed from the front and has been applied by a number of scholars in making linear measurements to analyze dental aesthetics. Beyond application to the teeth, a number of researchers have noted the appearance of the Golden Proportion in measuring the linear distances between certain points on the face. For example, some consider that in an attractive face the width of the mouth ill repose is roughly 1.618 multiplied by the width of the nose.

The Golden Proportion is discussed in U.S. Pat. Nos. 5,659,625 and 5,867,588 to Marquardt, which relate to methods for analyzing facial components. U.S. Pat. Nos. 4,416,063 and 4,768,953 to Nestor et al. disclose a caliper instrument for use in dentistry that is based on the Golden Proportion. U.S. Pat. No. 6,413,085 to Lee discloses a waxing guide for forming artificial teeth that employs the Golden Proportion. The guide has markings that indicate the desired relationship for an individual's anterior maxillary teeth, and this relationship is preferably in accordance with the Golden Proportion.

While these prior art patents are useful for their intended purposes, there remains a need in orthodontics and dentistry for making cosmetic change of an individual's smile according to that individual's facial parameters, including a means to determine a suitable size and position for an individual's teeth as they relate to facial landmarks.

SUMMARY OF THE INVENTION

In light of the foregoing, it would be advantageous to manage improvement of an individual's teeth by first determining what a suitable size and position for the teeth should be as they relate to landmarks of the individual's face, including the individual's eye landmarks. It would also be advantageous to utilize the individual's eyes as guides for determining a suitable size and position for the teeth within the jaw.

A first aspect of the invention provides a measuring device for determining orthodontic dimensions for an individual's teeth as they relate to facial landmarks, the device comprising: a gauge for determining a measurement between landmarks of the individual's face, the gauge comprising (a) a center marking line adapted to be centered over the individual's nasion and (b) a plurality of peripheral marking lines spaced at standard distances from the right and left of the center marking line.

A second aspect of the invention provides a method for determining orthodontic dimensions for an individual's teeth as they relate to facial landmarks, comprising the steps of: (a) centering a measuring device over the face of an individual using the nasion and the pupils of the individual as a guide, the device comprising a gauge for determining a measurement between landmarks of the individual's face, the gauge including a center marking line adapted to be centered over the individual's nasion and a plurality of peripheral marking lines spaced at standard distances from the right and left of the center marking line; (b) determining the distance from the center marking line to a landmark of the individual's left eye; (c) determining the distance from the center marking line to a landmark of the individual's right eye; (d) adding the two distances from steps (b) and (c) to obtain a measurement; (e) converting the measurement to an orthodontic dimension according to the Golden Proportion; and (f) using the determined orthodontic dimension in a treatment plan to alter the individual's teeth to modify their function or to improve their cosmetic appearance.

A third aspect of the invention provides a kit for determining orthodontic dimensions for an individual's teeth as they relate to facial landmarks, the kit comprising: a gauge for determining a measurement between landmarks of the individual's face, the gauge including a center marking line adapted to be centered over the individual's nasion and a plurality of peripheral marking lines spaced at standard distances from the right and left of the center marking line; a conversion chart for converting the measurement to an orthodontic dimension according to the Golden Proportion; and directions for using the gauge and the conversion chart to determine a suitable size and position for the individual's teeth.

The nature and advantages of the present invention will be more fully appreciated from the following drawings, detailed description and claims.

BRIEF DESCRIPTION OF THE DRAWINGS

The accompanying drawings illustrate embodiments of the invention and, together with a general description of the invention given above, and the detailed description given below, serve to explain the principles of the invention.

DETAILED DESCRIPTION OF THE INVENTION

As used herein, the phrase "bicuspid width" means the distance from the cusp tip of an individual's maxillary first bicuspid to the cusp tip of the individual's opposite maxillary first bicuspid.

The phrase "central incisor width" means the combined width of the anterior maxillary central incisors of an individual. There are typically two maxillary (i.e. upper) central incisors for an individual, and they typically are adjacent to one another with no teeth in between them. Central incisor width is typically the distance measured from the distal edge (i.e. lateral edge) of one central incisor to the distal edge of the other.

The phrase "cuspid width" means the distance from the cusp tip of an individual's maxillary cuspid to the cusp tip of the individual's opposite maxillary cuspid.

The term "gauge" means a measuring instrument for indicating or determining a distance between landmarks on an individual's face.

The terms "Golden Proportion" or "Golden Ratio" mean a mathematical relationship in which the sum of two quantities is to the larger quantity as the larger is to the smaller. That is, the Golden Proportion is a mathematical relationship between two linear distances from the division of a straight line in such a way that the shorter part (S) is to the longer part (L) as the longer part is to the whole (S+L). When this relationship applies, then the ratio of L to S is 1.618, or approximately 89/55. Further, L (the larger distance) divided by the larger ratio (for example 1.618) is equal to S (the smaller distance) divided by the smaller ratio (for example 1.0).

The term "measurement" as it pertains to a measurement determined by using the gauge of the invention, means a distance measured between two landmarks on an individual's face. As a non-limiting example, a measurement can be the distance measured from a landmark of one eye (e.g. the left eye) to a landmark of the other eye (e.g. the right eye) of an individual.

The term "nasion" (nay-zhun) means the intersection of the frontal and nasal bones of the human skull. Its manifestation on the visible surface of the face is a distinctly depressed area directly between the eyes, just superior to the bridge of the nose.

The phrase "orthodontic dimension" means the width between specific teeth, determined according to the Golden Proportion, which would be suitable for a specific individual. Accordingly, use of the gauge of the invention to obtain a measurement relating to that individual, along with a Golden Proportion conversion chart, allows a user to calculate a specific orthodontic dimension for that individual, and typically the dimension is one of the following: the central incisor width, the cuspid width, or the bicuspid width.

The term "suitable" as it pertains to an individual means appropriate or appropriately-sized according to what is generally considered a pleasant proportion for that individual's facial parameters, typically as determined by using the Golden Proportion.

Figure 1:
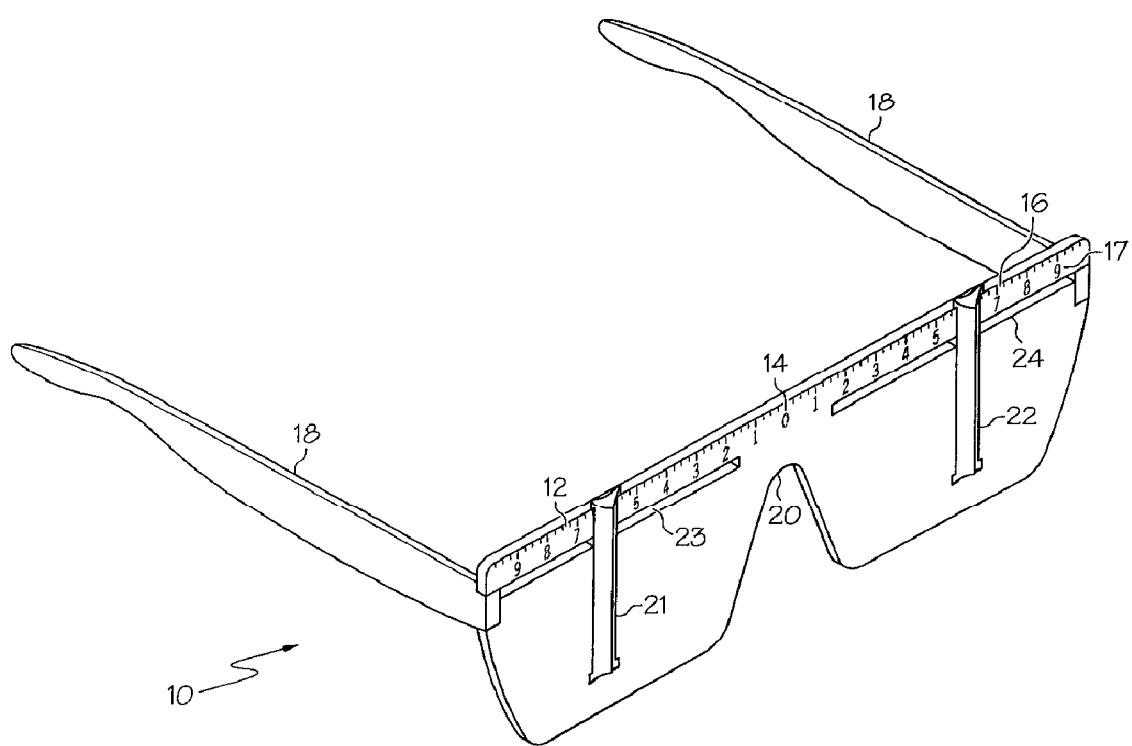
FIG. 1 is a perspective view of one embodiment of the measuring device of the invention.

The invention provides a measuring device, method and kit for determining a suitable size and position for an individual's teeth as they relate to facial landmarks. As illustrated in FIG. 1, the measuring device 10 can be in the shape of a pair of eyeglasses which has a gauge in the form of a transparent ruler body 12 with a center marking line 14. Peripheral marking lines 16 are spaced at standard distances from the right and left of the center marking line 14. Numbers 17 are shown below each of the marking lines, with the number zero (0) corresponding to the center marking line 14 and the remaining numbers corresponding to the standard distances of the peripheral marking lines from the right and left of the center marking line.

One embodiment of the measuring device 10 of the invention is illustrated in FIG. 1, in which the gauge or transparent ruler body 12 is wearable on an individual's head as a pair of eyeglasses. The eyeglasses include frames 18 attached to the ruler body 12. The ruler body 12 portion of the eyeglasses has a central bridge 20 for supporting the ruler body on the nose of the individual, a left vertical strut 21 slidably engaged within a left horizontal slot 23 in the ruler body, and a right vertical strut 22 slidably engaged within a right horizontal slot 24 in the ruler body 12. When the ruler body 12 is used to measure the eye landmarks of an individual, the center marking line 14 is centered over the central bridge 20, which is intended to be centered over the bridge of the individual's nose. As a non-limiting example, if the standard distances of the peripheral marking lines are in millimeters (mm), then the plurality of numbers typically range from zero (0) mm at the center marking line to up to sixty (60) mm to the right and left of the center marking line.

While the embodiment illustrated in FIG. 1 shows a ruler body connected to eyeglass frames, it is anticipated that goggle frames can also be used. In another embodiment of the eyeglasses (not shown), each of the vertical struts can be slidably engaged within two horizontal slots, i.e. an upper and a lower horizontal slot, to provide better control of the struts during measurement of the eye landmarks. For example, in addition to the top portion of the right vertical strut 22 being engaged in an upper right horizontal slot 24, a lower right horizontal slot (not shown) slidably engages the lower portion of the right vertical strut. In this embodiment, the upper and lower horizontal slots would typically be placed so that the individual's pupil is between the upper and lower slots, so that the eye landmarks are not obscured. Further, a second set of marking lines would be available below the lower slot to aid in precise measurement of the eye landmarks.

Figure 2:
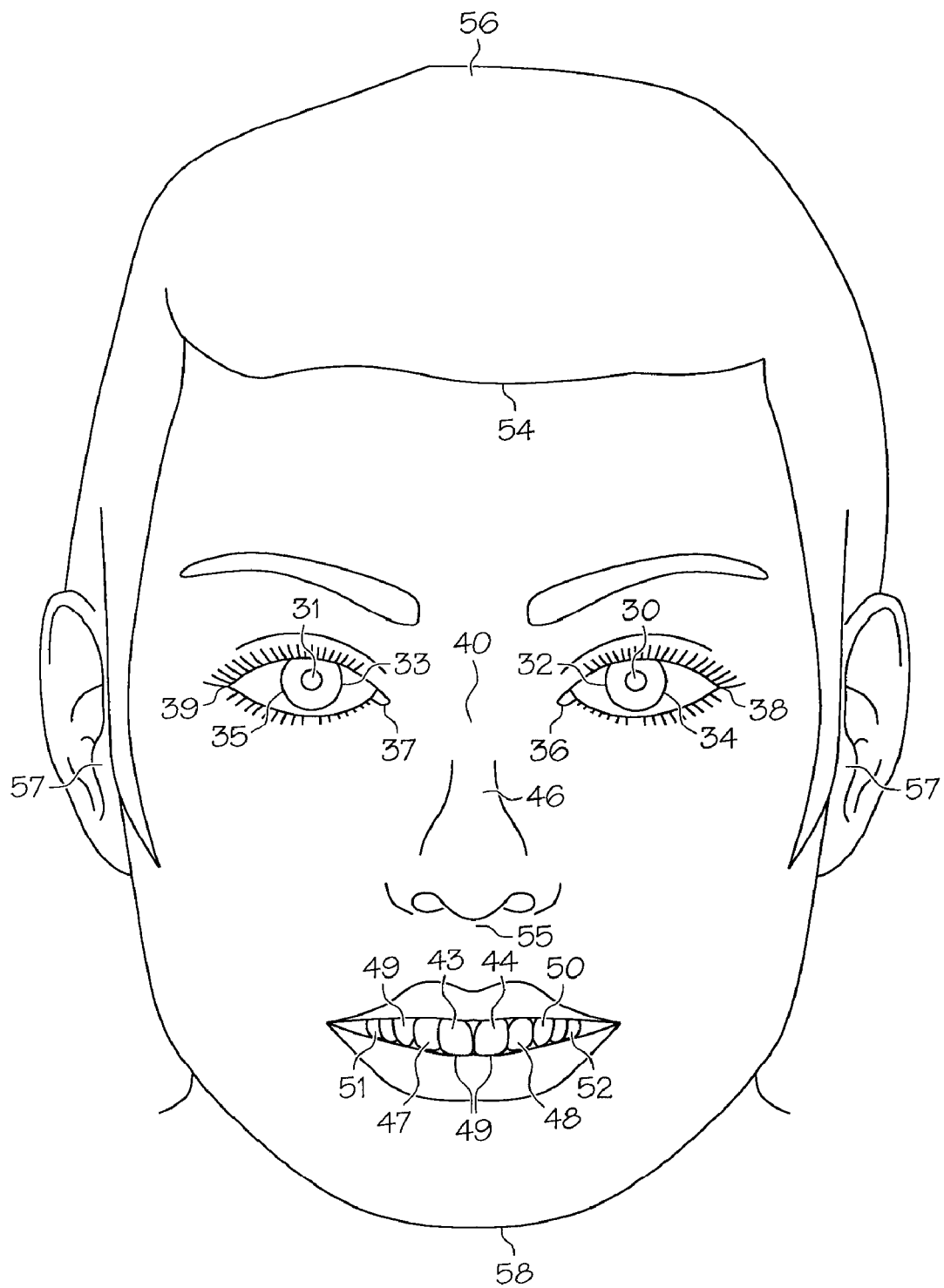
FIG. 2 is a frontal view of an individual's face illustrating landmarks which are used to take measurements according to the invention.

As shown in FIG. 2, eye landmarks of the individual which are typically used to make measurements are the following: the left pupil 30, the right pupil 31, the left inner iris 32, the right inner iris 33, the left outer iris 34, the right outer iris 35, the left inner canthus 36, the right inner canthus 37, the left outer canthus 38, and the right outer canthus 39. Also, the nasion 40, which is located just above the bridge of the nose 46, is typically used as a zero point to center the gauge of the invention.

Typical orthodontic dimensions taken by an orthodontist using the present invention are one of the following: the central incisor width, the cuspid width, and the bicuspid width, as defined above. That is, to provide a suitable central incisor width for an individual, the orthodontist typically wants to determine a suitable combined width of an individual's right and left anterior maxillary central incisors, 43, 44, measuring from the distal edge of the right central incisor 43 to the distal edge of the left central incisor 44. While the lateral incisors 47, 48 are an important part of an individual's smile, typically the orthodontist next prefers to measure the cuspid width, which is the distance from the cusp tip of the right maxillary cuspid 49 to the cusp tip of the left maxillary cuspid 50. The bicuspid width is also important and is the distance from the cusp tip of the right maxillary first bicuspid 51 to the cusp tip of the left maxillary first bicuspid 52. Other landmarks which are commonly used include the tips of the central incisors 53, the hairline 54, the columella or base of the nose 55, the top of the head 56, the tragus of each ear 57, and the chin 58. See FIG. 4 for an example of how these landmarks are used according to the Golden Proportion.

In use, the vertical struts 21, 22 of the eyeglasses of FIG. 1 are able to slide along the length of the horizontal slots 23, 24 to align with eye landmarks of the individual and obtain a measurement. To take a measurement, a user first centers the measuring device of the invention over the nasion Oust above the bridge) of the individual's nose 46 and then determines the distance from the center marking line 14 to a landmark of the individual's right eye, as well as the distance from the center marking line to a landmark of the individual's left eye. The two distances are then added together. The number obtained from adding the two distances together is known herein as a "measurement," as defined above. After a measurement is taken to determine the distance between the selected eye landmarks, a conversion chart, such as that shown in Table 1, is used to convert the measurement to an orthodontic dimension according to the Golden Proportion.

For purposes of the present invention, the conversion chart of Table 1 includes pre-determined measurements which correspond to pre-determined suitable orthodontic dimensions, using the Golden Proportion. In the top row, the bold numbers 2.618, 1.618, 1.0 and 0.618 represent ratios or proportions according to the Golden Proportion, and the numbers beneath these ratios represent suitable measurements according to the Golden Proportion. These measurements can be in millimeters, centimeters, inches, etc.

The numbers beneath the ratios (ratios are in bold print) of Table 1 have been determined by using the following Golden Proportion formula: L (the larger distance) divided by the larger ratio is equal to S (the smaller distance) divided by the smaller ratio, where L is typically a known number (obtained by measurement) and located under the column of the larger ratio, and S is the corresponding suitable orthodontic measurement according to the Golden Proportion and located under the column of the smaller ratio.

TABLE 1

| 2.618 | 1.618 | 1.0 | 0.618 |
| --- | --- | --- | --- |
| 30.00 | 18.54 | 11.46 | 7.08 |
| 32.00 | 19.77 | 12.22 | 7.55 |
| 34.00 | 21.01 | 12.98 | 8.03 |
| 36.00 | 22.25 | 13.75 | 8.50 |
| 38.00 | 23.48 | 14.51 | 8.97 |
| 40.00 | 24.72 | 15.28 | 9.44 |
| 42.00 | 25.96 | 16.04 | 9.92 |
| 44.00 | 27.19 | 16.80 | 10.39 |
| 46.00 | 28.43 | 17.57 | 10.86 |
| 48.00 | 29.66 | 18.33 | 11.33 |
| 50.00 | 30.90 | 19.10 | 11.80 |
| 52.00 | 32.14 | 19.86 | 12.28 |
| 54.00 | 33.37 | 20.62 | 12.75 |
| 56.00 | 34.61 | 21.39 | 13.22 |
| 58.00 | 35.84 | 22.15 | 13.69 |
| 60.00 | 37.08 | 22.92 | 14.16 |
| 62.00 | 38.32 | 23.68 | 14.64 |
| 64.00 | 39.55 | 24.44 | 15.11 |
| 66.00 | 40.79 | 25.21 | 15.58 |
| 68.00 | 42.02 | 25.98 | 16.04 |
| 70.00 | 43.26 | 26.74 | 16.52 |
| 72.00 | 44.50 | 27.50 | 17.00 |
| 74.00 | 45.73 | 28.26 | 17.46 |
| 76.00 | 46.97 | 29.03 | 17.94 |

TABLE 1-continued

| 2.618 | 1.618 | 1.0 | 0.618 |
| --- | --- | --- | --- |
| 78.00 | 48.20 | 29.79 | 18.41 |
| 80.00 | 49.44 | 30.55 | 18.89 |
| 82.00 | 50.67 | 31.32 | 19.35 |
| 84.00 | 51.91 | 32.08 | 19.83 |
| 86.00 | 53.15 | 32.85 | 20.30 |
| 88.00 | 54.38 | 33.61 | 20.77 |
| 90.00 | 55.62 | 34.37 | 21.25 |
| 92.00 | 56.85 | 35.13 | 21.72 |
| 94.00 | 58.09 | 35.90 | 22.19 |
| 96.00 | 59.32 | 36.66 | 26.66 |
| 98.00 | 60.56 | 37.43 | 23.13 |
| 100.00 | 61.80 | 38.19 | 23.61 |

For example, looking at Table 1, assume that a measurement is taken that measures 100 cm, and the ratio for using this measurement to determine a suitable orthodontic dimension is 2.618 to 1.618. Using the number 100 as L (or large measurement), which, looking at Table 1, is the last measurement under the column for the larger ratio 2.618, the corresponding suitable orthodontic measurement, or S, under the column for the smaller ratio of 1.618 can be determined. That is, if L=100, then 100 divided by 2.618 (the larger ratio) is equal to S divided by 1.618 (the smaller ratio). This formula can be rearranged to determine the value of S, such that S=[(100 times 1.618) divided by 2.618], or S=61.80. Similarly, to determine the corresponding number (S) under the column for the smaller ratio 1.0, L is now equal to 61.80, the larger ratio is 1.618, and the smaller ratio is 1.0, such that S=[(61.80 times 1.0) divided by 1.618], or S=38.19. In this manner the measurements for Table 1 can be determined.

Table 1 can thus be used to determine a corresponding suitable proportion for a particular measurement taken on an individual. For example, it has been determined that the ratio of the distance between an individual's inner iris' to the central incisor width is 2.618 to 1, such that the inner iris width is 2.618 times the central incisor width. Thus, the measured distance from the left inner iris to the right inner iris would be located under the 2.618 column of Table 1, and the number under the 1.0 column would represent a suitable (according to the Golden Proportion) dimension for that individual's central incisor width (measuring from the distal edge of the right central incisor to the distal edge of the left central incisor). Thus using Table 1, if the individual's inner iris width is 30 mm (located under the 2.618 column of Table 1), then a suitable central incisor width for that individual would be 11.46 mm (located under the 1.0 column of Table 1). If the inner iris width is 50 mm, then using the conversion chart in Table 1 the measurement of 50.00 under the 2.618 column corresponds to a suitable orthodontic dimension for the central incisor width of 19.10 mm under the 1.0 column.

Similarly, the ratio of the inter-pupil distance (i.e. the distance between the left pupil to the right pupil) and the cuspid width is 2.618 to 1.618. So, the inter-pupil distance is first located under the 2.618 column of Table 1, and the converted orthodontic dimension for the cuspid width of that individual would be found under the 1.618 column of Table 1. Accordingly, if an individual's inter-pupil distance is 38 mm and one would like to determine a suitable cuspid width for that individual, it can be found in Table 1 by locating the number under the 1.618 column that corresponds to 38.00 under the 2.618 column, such that that individual's suitable orthodontic measurement for cuspid width is 23.48 mm. So, if the measurement from the left pupil to the right pupil is 54.00 mm, which is found under the 2.618 column of Table 1, then the corresponding cuspid width would be 33.37 mm, (found under the 1.618 column).

For bicuspid width, either the distance between the left outer iris to the right outer iris, or the distance between the left pupil and the right outer canthus is measured and located under the 2.618 column, and the ratio of this measurement to the bicuspid width is 2.618 to 1.618. Thus, if the measurement from the left outer iris to the right outer iris is 58.00 mm (found in the 2.618 column), then, looking under the 1.618 column, the corresponding bicuspid width is 35.84 mm. In calculating the orthodontic dimensions using these measurements, if any measurement taken should be an integer, such as 57.60 mm, it is recommended that the number be rounded up or down to the nearest even number.

Indeed, an orthodontist trained to use the measuring device and conversion chart of the invention can use the predicted orthodontic dimensions for an individual in a treatment plan to alter the individual's teeth, to modify their function, or to improve their cosmetic appearance. The widths of the teeth can thus be altered according to methodologies known in the art, such as bonding, laminates, crowns, etc., to achieve the desired Golden Proportion dimensions. The specific values of these widths have been calculated, which are found in the chart of Table 1.

Figure 3:
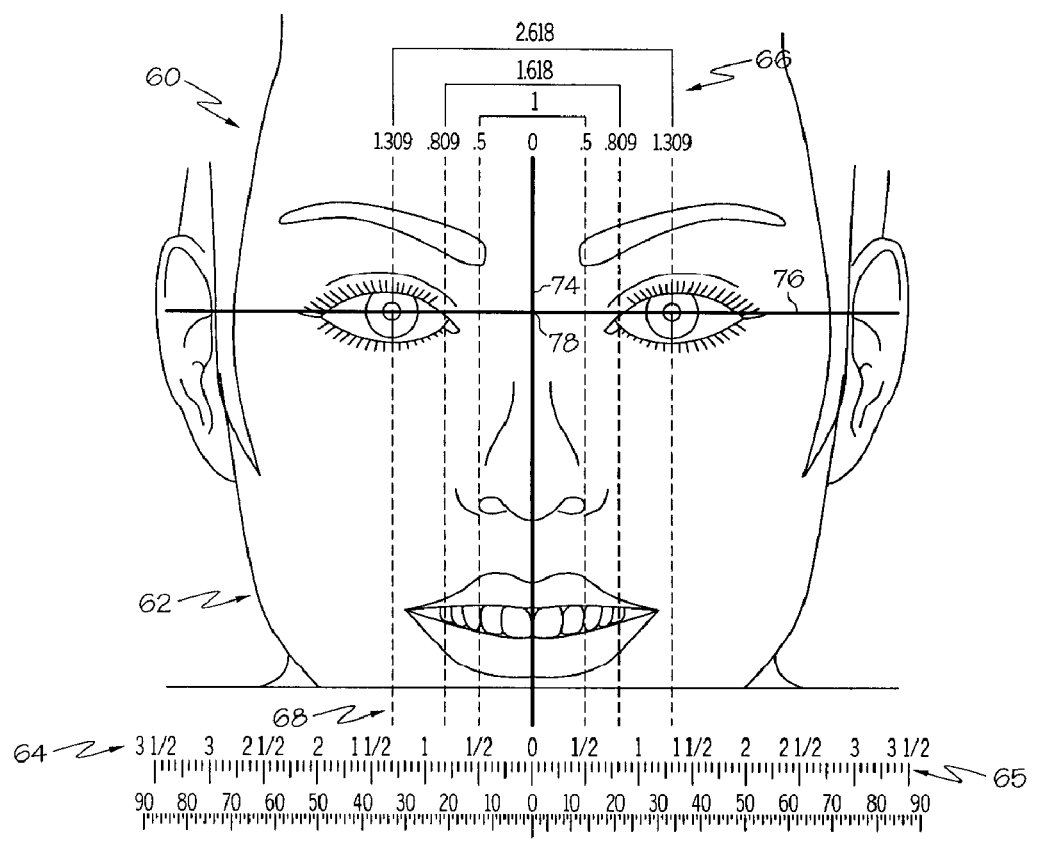
FIG. 3 is a frontal view of one embodiment of the measuring device of the invention.

FIG. 3 illustrates another embodiment of a gauge of the present invention, and includes a facial grid 60 for determining an orthodontic dimension. In this embodiment, a photograph 62 of the individual has a ruler 64 as part of a measuring grid superimposed over it. The measuring grid typically includes standardized marking lines 65 which are part of the ruler 64, Golden Proportion ratios 66, vertical dashed lines 68, and a central vertical line 74. As illustrated, the ruler 64 is typically located below the face of the photograph 62, and is centered beneath the central vertical line 74 which passes through the vertical center of the individual in the photograph 62. A horizontal line 76 is also illustrated, which is aligned with the pupils of the individual's eyes and is perpendicular to the central vertical line 74. The central line 74 and the horizontal line 76 intersect at a zero point 78, which is typically at the nasion, between the eyes of the individual and over the bridge of the nose. Ratios 66, relating to the Golden Proportion, are located above the photograph 62 and indicate suitable Golden Proportion ratios for landmarks measured a distance outward from the central vertical line 74. Vertical dashed lines 68 extend through the face of the photograph from the ratios 66 and end over the ruler 64, so that the ratios can be converted into distances. For convenience, in FIG. 3 the distances of various facial landmarks from the central vertical line 74 are displayed above the photograph and below the ratios 66 (i.e. 1.309, 0.809 and 0.5).

To take a measurement using a gauge in the form of the facial grid 60 of FIG. 3, typically a user first takes a photograph 62 of the individual and then centers the ruler 64 with its marking lines 65 beneath the central vertical line 74. The central vertical line 74 and the central horizontal line 76 meet at the zero point 78, which is typically located at the center of the photograph 62, i.e. the zero point is centered directly between the pupils at the nasion, just above the bridge of the nose of the photograph. More specifically, the facial grid 60 is typically centered by placing the zero point 78 over the photograph 62 by aligning the vertical line 74 between the pupils and the horizontal line 76 over the nasion. The combination of the photograph 62 with a measurement grid, the measurement grid typically including the ruler 64, the ratios 66, the central vertical line 74, the horizontal line 76, the zero point 78, and the vertical dashed lines 68, amounts to a facial grid 60.

Creation of this facial grid can typically be performed on a computer onto which these elements have been downloaded. Alternatively, a transparent ruler can be placed over a paper photograph of the individual and the ratios, the central vertical line, the horizontal line, the zero point and the vertical dashed lines can be drawn in or added.

Once the facial grid is made, the user can then determine suitable proportions for the individual's teeth and facial features. The ratios 66, which are spaced at pre-determined intervals from the zero point 78, help determine a suitable distance from the zero point 78 that the individual's teeth (and facial landmarks) should be. Thus, the facial grid 60 can be used to determine a suitable orthodontic dimension for an individual, according to the Golden Proportion. Using this facial grid, the orthodontist can determine any individual's orthodontic dimensions, as dictated by using the Golden Proportion, by taking photographs of the individual and superimposing the measurement grid (including the ruler 64, the ratios 66, the central vertical line 74, the horizontal line 76, the zero point 78, and the vertical dashed lines 68) over the photograph. The orthodontist can then apply these measured orthodontic dimensions to create crowns, apply braces, etc. to make the individual's teeth appear to be what is considered attractive according to the Golden Proportion.

Figure 4:
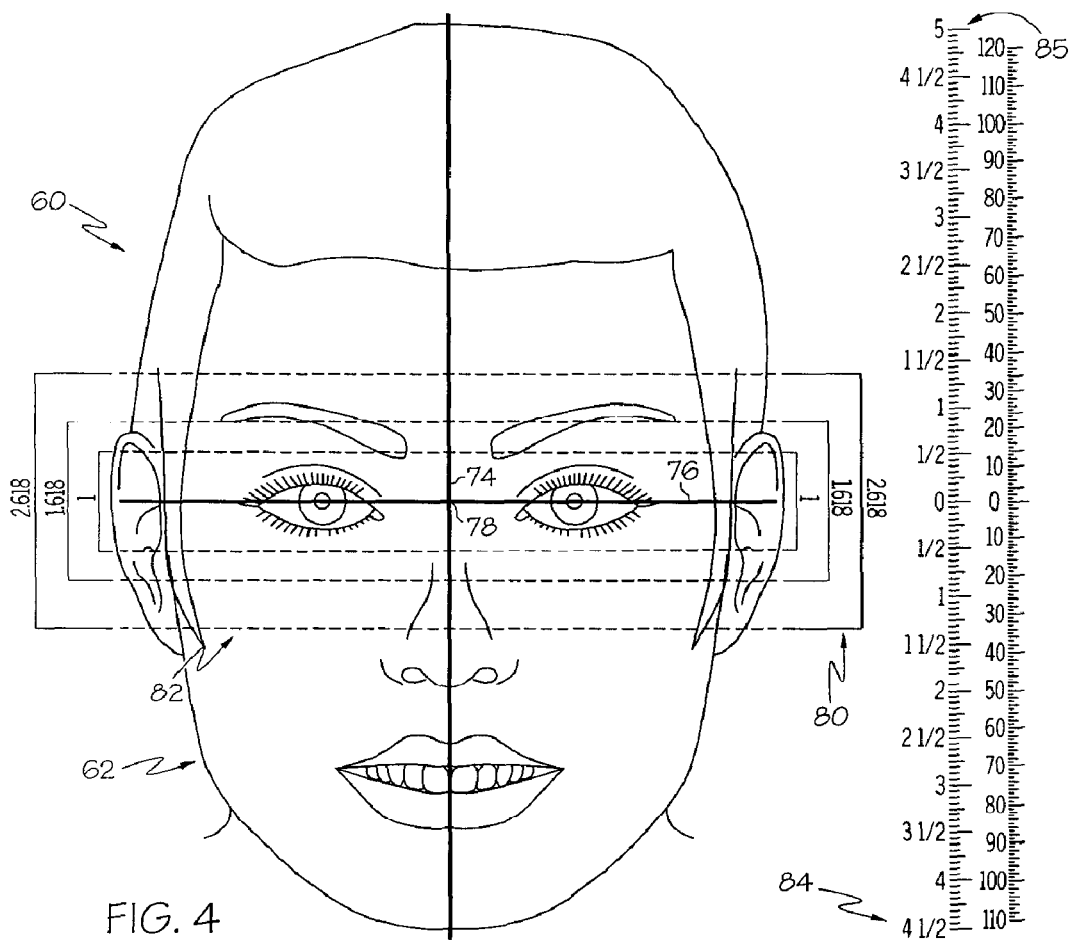
FIG. 4 is a frontal view of one embodiment of the measuring device of the invention.

FIG. 4 illustrates a similar facial grid as in FIG. 3; however the ruler 84 and markings 85 are placed vertically along one side of the face of the photograph 62. As illustrated, the ruler 84 is typically centered according to the horizontal line 76, which is aligned with the pupils of the individual's eyes and is perpendicular to the central vertical line 74. Ratios 80, relating to the Golden Proportion, indicate suitable Golden Proportion ratios for landmarks measured a distance outward from the horizontal line 76. Horizontal dashed lines 82 extend through the face of the photograph from the ratios 80. The ruler can be used to convert these ratios into distances. For example, using the ruler of FIG. 4 one can determine where the incisor tips should be located on a vertical plane, or the height of the incisors in relation to the eyes.

More specifically, one can obtain a measurement from the inner canthus to the base of the nose (i.e. the columella 55 of FIG), and use this measurement to determine a suitable distance for that individual from the base of the nose to the tip of the central incisors (also known as the incisal edge). In this example the first measurement (from the inner canthus to base of the nose) would be located under the 1.618 column of Table 1, and the distance from the base of the nose to the incisal edge would be located under the 1.0 column. Similarly, the ratio of 1.618 to 1.0 can be used with the following: a measurement from the hairline to the inner canthus (1.618) can determine the suitable distance from the inner canthus to the base of the nose (1.0); a measurement from the base of the nose to the incisal edge (1.0) can determine a suitable distance from the incisal edge to the chin (1.618).

Regarding the facial grids of FIGS. 3 and 4, to ensure that the proportionality of the photograph in relation to the individual's face is correct for taking meaningful measurements, an eyeglass gauge (FIG. 1) of the invention can first be used to take a measurement of at least one eye landmark, preferably between the individual's pupils, to create a standard to which the facial grid 60 can be compared. For example, if the eyeglasses measure 50.00 mm from one inner iris to the other, then the photograph can be proportionally manipulated so that the measurement from inner iris to inner iris in the photograph is also 50.00 mm. The photograph can also be sized to measure one-half the actual size, e.g. at 25.00 mm, just as long as there is proportionality between the individual's face and the photograph. In this manner, a user of the invention can take any picture of the individual's face and manipulate it so that a ruler can be placed over the face of the individual in the photograph for meaningful measurements to be taken.

The measuring device of the invention can be part of a kit for determining a suitable size and position for an individual's teeth as they relate to facial landmarks. Such a kit typically comprises a gauge such as that of the measuring device 10 of FIG. 1, a conversion chart such as that of Table 1 for converting measurements to an orthodontic dimension according to the Golden Proportion, and directions for using the gauge and the conversion chart to determine a suitable size and position for the individual's teeth. The directions are typically instructions comprising: (a) centering the gauge over the face of an individual by using the nasion and the pupils of the individual as a guide; (b) determining the distance from the center marking line to a landmark of the individual's left eye; (c) determining the distance from the center marking line to a landmark of the individual's right eye; adding the two distances from steps (b) and (c) to obtain a measurement; and (d) using the conversion chart to convert the measurement to an orthodontic dimension according to the Golden Proportion.

While the present invention has been illustrated by the description of embodiments and examples thereof, it is not intended to restrict or in any way limit the scope of the appended claims to such detail. Additional advantages and modifications will be readily apparent to those skilled in the art. Accordingly, departures may be made from such details without departing from the scope or spirit of the invention.

What is claimed is:

1. A measuring device for determining orthodontic dimensions for an individual's teeth as they relate to facial landmarks, the device comprising:
  a gauge for determining a measurement between landmarks of the individual's face when worn, the gauge having a transparent ruler body and comprising (a) a center marking line adapted to be centered over the individual's nasion; (b) a plurality of peripheral marking lines spaced at standard distances from the right and left of the center marking line; and (c) a central bridge for supporting the ruler body on the nose of the individual;
  frames attached to the transparent ruler body of the gauge;
  a left vertical strut slidably engaged within a left horizontal slot in the ruler body, which aligns with landmarks of the left eye of the individual; and
  a right vertical strut slidably engaged within a right horizontal slot in the ruler body, which aligns with landmarks of the right eye of the individual,
  wherein the left and right vertical struts slide within the left and right horizontal slots at least from the inner canthus to the outer canthus of the individual's left and right eyes, respectively.

2. The measuring device of claim 1, wherein the standard distances of the peripheral marking lines are measured according to distances selected from the group consisting of micrometers, millimeters, centimeters, and inches.

3. The measuring device of claim 1, wherein the frames are selected from the group consisting of eyeglass frames and goggle frames.

4. A kit for determining orthodontic dimensions for an individual's teeth as they relate to facial landmarks, the kit comprising:
  a) a transparent ruler body wearable on the individual's head for determining a measurement between landmarks of the individual's face, the ruler body including:
    i) a center marking line adapted to be centered over the individual's nasion, a plurality of peripheral marking lines spaced at standard distances from the right and left of the center marking line;
    ii) frames adapted to be worn on the head of the individual, the ruler body being attached to the frames and further including a central bridge for supporting the ruler body on the nose of the individual;
    iii) a left vertical strut slidably engaged within a left horizontal slot in the ruler body, the left vertical strut adapted to align with landmarks of the left eye of the individual; and
    iv) a right vertical strut slidably engaged within a right horizontal slot in the ruler body, the right vertical strut adapted to align with landmarks of the right eye of the individual, wherein the horizontal slots allow the vertical struts to slide at least from the inner canthus to the outer canthus of the individual's eyes;
  b) a conversion chart for converting the measurement to an orthodontic dimension according to the Golden Proportion; and
  c) directions for using the gauge and the conversion chart to determine a suitable size and position for the individual's teeth.

5. The kit of claim 4, wherein the directions are instructions comprising the steps of:
  a. centering the gauge over the face of an individual by using the nasion and the pupils of the individual as a guide;
  b. determining the distance from the center marking line to a landmark of the individual's left eye, wherein the landmark of the left eye is selected from the group consisting of the left pupil, the left inner iris, the left outer iris, the left inner canthus, and the left outer canthus;
  c. determining the distance from the center marking line to a landmark of the individual's right eye, wherein the landmark of the right eye is selected from the group consisting of the right pupil, the right inner iris, the right outer iris, the right inner canthus, and the right outer canthus;
  d. adding the two distances from steps (b) and (c) to obtain a measurement; and
  e. converting the measurement to an orthodontic dimension according to the Golden Proportion.

* * * * *